United States Patent
Gilby

(10) Patent No.: US 7,362,429 B2
(45) Date of Patent: Apr. 22, 2008

(54) OPAQUE ADDITIVE TO BLOCK STRAY LIGHT IN AMORPHOUS FLUOROPOLYMER LIGHT-GUIDING FLOWCELLS

(75) Inventor: Anthony C. Gilby, Foxborough, MA (US)

(73) Assignee: Waters Investments Limited, New Castle, DE (US)

( * ) Notice: Subject to any disclaimer, the term of this patent is extended or adjusted under 35 U.S.C. 154(b) by 322 days.

(21) Appl. No.: 10/911,126

(22) Filed: Aug. 4, 2004

(65) Prior Publication Data
US 2005/0078308 A1    Apr. 14, 2005

(51) Int. Cl.
G02B 6/00      (2006.01)
G01N 1/10      (2006.01)
G01N 21/47     (2006.01)
G01N 21/05     (2006.01)
G01N 21/85     (2006.01)

(52) U.S. Cl. .............. 356/246; 356/436; 356/446; 356/441; 356/442; 385/144; 385/145

(58) Field of Classification Search .............. 356/246, 356/436, 446, 441–442; 385/145, 144
See application file for complete search history.

(56) References Cited

U.S. PATENT DOCUMENTS

| 5,184,192 | A |  | 2/1993 | Gilby |  |
|---|---|---|---|---|---|
| 5,430,541 | A |  | 7/1995 | Sapp |  |
| 5,434,664 | A |  | 7/1995 | Sapp |  |
| 5,444,807 | A | * | 8/1995 | Liu | ............................ 385/125 |
| 6,020,207 | A | * | 2/2000 | Liu | ............................ 436/164 |
| 6,188,813 | B1 |  | 2/2001 | Dourdeville et al. |  |
| 6,199,257 | B1 |  | 3/2001 | Munk et al. |  |
| 6,300,638 | B1 |  | 10/2001 | Groger et al. |  |
| 6,385,380 | B1 |  | 5/2002 | Friedrich et al. |  |
| 6,388,746 | B1 |  | 5/2002 | Erikson et al. |  |
| 6,507,688 | B1 |  | 1/2003 | Nath |  |
| 6,580,507 | B2 | * | 6/2003 | Fry et al. | ..................... 356/436 |
| 6,678,051 | B2 | * | 1/2004 | Gerner et al. | ............... 356/436 |
| 6,734,961 | B2 | * | 5/2004 | Gerner et al. | ............... 356/246 |
| 6,867,857 | B2 | * | 3/2005 | Hobbs | ........................ 356/246 |
| 2002/0071123 | A1 |  | 6/2002 | Miller et al. |  |
| 2002/0126276 | A1 |  | 9/2002 | Eriksson et al. |  |
| 2003/0049841 | A1 | * | 3/2003 | Short et al. | ................. 435/449 |
| 2006/0139632 | A1 |  | 6/2006 | Gerner et al. |  |

OTHER PUBLICATIONS

Datta, et al., Microfabrication and Characterization of Teflon AF-Coated Liquid Core Waveguide Channels in Silicon, IEEE Sensors, Dec. 2003, vol. 3, No. 6.*
U.S. Appl. No. 11/821,905, filed Jun. 26, 2007, A. Jeannotte.

* cited by examiner

*Primary Examiner*—F L. Evans
*Assistant Examiner*—Bryan J Giglio
(74) *Attorney, Agent, or Firm*—Edwards Angell Palmer & Dodge LLP; Peter C. Lauro, Esq.

(57) ABSTRACT

The present invention is directed to the use of a light absorbing wall material to eliminate stray light paths in light-guiding structures, such as those used for HPLC absorbance detection. More specifically, the present invention relates to the use of carbon-doped Teflon® AF, or "black Teflon® AF," for all or part of the walls of a light-guiding flowcell adapted for use in HPLC absorbance detection.

7 Claims, 5 Drawing Sheets

OPAQUE ADDITIVE TO BLOCK STRAY LIGHT IN AMORPHOUS FLUOROPOLYMER LIGHT-GUIDING FLOWCELLS

CROSS REFERENCE TO RELATED APPLICATIONS

This application is a continuation of PCT International Patent Application No. PCT/US03/05811, filed Feb. 25, 2003, abandoned, which U.S. Provisional Patent Application No. 60/359,354, filed Feb. 25, 2002. The contents of these applications are incorporated herein by reference.

BACKGROUND OF THE INVENTION

The present invention relates generally to the use of a light absorbing wall material to eliminate stray light paths in light-guiding applications, such as High Performance Liquid Chromatography (HPLC), and Capillary Zone Electrophoresis (CZE) spectroscopic analysis.

Systems for light absorption detection generally comprise four basic components; a light source, a means for selecting wavelengths to be used, a light-guiding vessel, typically in the form of a hollow tube or capillary through which a sample to be analyzed and light are passed (a flowcell), and a light detector which measures the amount of light transmitted through the flowcell. Large optical throughput can be achieved when the light is guided along the capillary similar to the way light is guided along an optical fiber.

A flowcell must be constructed from materials that are resistant to the solutions encountered in liquid chromatography or CE. To achieve high sensitivity to small concentrations of analyte, the cell must have a high optical throughput and a long pathlength. If the quantity of analyte is small and capillary separation techniques are used, the volume of the cell must also be small, otherwise band spreading and loss of chromatographic resolution occurs. The transmittance, T, of light through such a system filled with a light absorbing sample is determined in accordance with Beer's law:

$$T = \frac{I}{I_0} \tag{1a}$$

$$A = \log_{10}\left(\frac{I_0}{I}\right) = \varepsilon b c \tag{1b}$$

where $I_0$ is the light exiting the flowcell when it is filled with clear mobile phase and I is the light power exiting the flowcell when analyte is present. b is the path length of the flowcell conventionally expressed in centimeters, c is the analyte concentration in M or moles/liter and $\varepsilon$ is the molar absorptivity expressed in units of $cm^{-1}(moles/liter)^{-1}$. A is the absorbance, a dimensionless number expressed in absorbance units (au).

The requirement for high light throughput and long pathlength is illustrated by differentiating equation (1b).

$$\Delta c = \frac{\Delta A}{b\varepsilon} \tag{1c}$$

$\Delta c$ represents the smallest analyte concentration that can be detected and $\Delta A$ the corresponding smallest change in absorbance that can be measured. This represents the noise at the absorbance baseline, the output of the absorbance detector.

As illustrated by equation (1b), low absorbance noise requires a high light signal $I_0$ and low noise in the measurement of I, i.e. a high signal-to-noise (S/N) ratio in the raw transmittance measurement. In a well-designed detector, shot noise, which is proportional to the square root of the light signal, dominates, so high S/N requires high light throughput.

Light-guiding flowcells enable low volume cells to be constructed with high light throughput and long path length. The liquid sample is contained in a tube of material having a lower refractive index (RI) than the mobile phase. Light is introduced into one end of the tube and propagates down the axis of the tube making multiple internal reflections before emerging at the other end. The liquid is analogous to the core of an optical fiber and the material of the tube is analogous to the cladding. The condition for light guiding is that the rays incident on the liquid/wall boundary do so at an angle of incidence greater than the critical angle $\theta_c$.

$$\theta_c = \sin^{-1}\frac{n_2}{n_1} \tag{2a}$$

where $n_1$ is the RI of the liquid, and $n_2$ is the RI of the wall of the flowcell.

The numerical aperture (NA) of the guided beam is given by:

$$NA = \sin^{-1}\phi = (n_1^2 - n_2^2)^{1/2} \tag{2b}$$

Where $\phi$ is the largest angle, between a ray entering the cell from air and the cell axis, which meets the guiding condition. The guiding mechanism is termed total internal reflection (TIR)

Recently, flowcells having an inner surface of an amorphous fluoropolymer material that has an index of refraction lower than that of common chromatography solvents, e.g. water, have enabled light-guiding flowcells to be constructed.

Light introduced along the axis of the tube is guided in the fluid by total internal reflection at the fluid wall boundary. The amorphous fluoropolymer material Teflon® AF 1600 and 2400 are preferred tube materials because they are transparent throughout the visible and ultraviolet spectrum, they have an unusually low refractive index (1.31 and 1.29 respectively) and are chemically inert. As a comparison, the RI of water at the same wavelength is 1.333. All common solvents (as methanol/water mixtures and acetonitrile) have a higher RI than water and therefore also Teflon® AF. Only pure methanol has an index slightly below water, but still above that of Teflon® AF. Even at different wavelengths, the fluoropolymers retain the RI advantage.

However, it is difficult to construct a cell with amorphous fluoropolymer walls without some light entering the end cross-section of the wall, or some light 18 being scattered into the wall from the liquid, or some light 18 entering the fluid from the walls after bypassing part or all of the sample fluid. These aberrant light paths result in a stray light background and inaccuracy in the readings, limiting the linearity and dynamic range of a detector that is supposed to receive only light that has passed through the liquid.

One strategy to control stray light positions opaque masks between the walls and the light, but the small diameter tubes of HPLC and CZE equipment makes the alignment of such masks difficult and time consuming. A second strategy to control stray light supplies entering light through an optical fiber having an OD that fits between the walls, but the amount of light coupled into the liquid is reduced geometrically by the reduced area The difficulty of controlling stray light becomes greater as fluid cross-sections are made smaller. For capillary HPLC or CZE detection, a fluid channel ID of 100 µm or less is needed to create a small volume flowcell, with sufficient pathlength to preserve analytical sensitivity. A better way is needed to fabricate light guiding flowcells to avoid the difficulties of controlling stray light outlined above

SUMMARY OF THE INVENTION

The present invention provides an apparatus and method for controlling stray light in vessels having small cross sections, used especially for light absorption measurements.

In a preferred application, the vessel is a flowcell receiving analyte from a HPLC apparatus. One embodiment is a device for receiving one or more samples and measuring light emitted or refracted therefrom. This device comprises a vessel with a cavity for containing a sample during a measuring process, where the vessel comprises at least one wall in fluid contact with the sample, the wall having a composition having an index of refraction lower than the index of refraction of a fluid in the sample. Further the wall has an absorption coefficient sufficient to substantially attenuate light propagating through the wall and the vessel has at least one means for passage of transmitting light, wherein light within the cavity is guided by attenuated total reflection into the sample. By judicious choice of the wall absorption coefficient, the light guided through the fluid by internal reflection is only minimally attenuated. The means for means for passage of transmitting light may be an opening, a window, a lens or an optical fiber. A preferred material for the wall is Teflon® AF fluoropolymer doped with a black dopant such as carbon black.

Another embodiment is a light-guiding apparatus comprising a fluid channel bounded by at least one wall, the composition of the wall having an index of refraction lower than the index of refraction of a fluid in the fluid channel and having an absorption coefficient sufficient to substantially attenuate light propagating through the walls. The apparatus further comprises an entrance and exit for light, the entrance and exit perpendicular to an axis of the channel and fluid inlet and outlet ports, whereby the walls and fluid effect guiding of the light by attenuated total reflection, the walls having minimal absorptive effect on the guided light. The walls have an absorption coefficient in the range of 0.1 to 100 $mm^{-1}$ at a wavelength within the wavelength range of UV, visible and near IR. A preferred material for the walls is Teflon® AF fluoropolymer doped with a black dopant such as carbon black. A concentration of carbon black between 0.01% and 1% by weight of the fluoropolymer is sufficient to absorb stray light.

Another embodiment is an apparatus for housing a liquid sample and for exposing the liquid sample to light. The apparatus comprises a conduit having a wall formed of an amorphous fluoropolymer having a refractive index less than the refractive index of water and having an absorption coefficient of a magnitude such that when the conduit is filled with water, visible and ultra-violet light can be transmitted, substantially without loss, along the axis of the conduit by attenuated total reflection but visible and ultraviolet light are substantially completely absorbed in passage through the walls of the conduit.

A method of performing photometric analysis of a liquid sample with improved linearity of detection comprises introducing the liquid sample into a conduit having a wall formed of an amorphous fluoropolymer having a refractive index less than a refractive index of water and having an absorption coefficient sufficient to substantially attenuate light propagation through the wall, shining light axially onto the conduit filled with sample liquid, receiving light transferred through the liquid sample at a detector; and determining the concentration of the sample in the liquid by measuring the light absorption of the sample. When light is axially shone onto the conduit filled with sample liquid, light transferred through the liquid sample is detected and the concentration of sample in the liquid is determined. Alternately the sample concentration can be determined used the emitted florescence or Raman scattered light.

A set of light-guiding flowcells for a fluid comprises a set of channels formed in a substrate of material having an index of refraction lower than the index of the fluid and an absorption coefficient sufficient to substantially attenuate light propagating through the material. A set of channel covers formed in a section of material having an index of refraction and absorption coefficient identical to the substrate of material is fixed to the set of channels forming a set of covered channels. At least one covered channel, or interconnected set of covered channels, has a fluid inlet and outlet port. At least one covered channel has a source of light at a light entrance end and has a light exit end. The at least one covered channel and fluid therefore effect guiding of the light by attenuated total reflection and the at least one covered channel has minimal absorptive effect on the light guided by internal reflection. A covered channel may be configured as a separation column. The interconnected channels for perform analysis on a fluid passing therethrough when the output of the separation column is connected to the light-guiding channel, where the light exit end is connected to a detector external to the set of flowcells.

A typical use for the invention is in a flowcell for HPLC or CE absorbance detection where the flowcell is constructed from a hollow tube of low index material such as Teflon® AF 2400, darkened wherein the wall material is sufficiently absorbing to block light transmission through the wall. At the same time, the absorption by the wall is low enough that light guiding is substantially unaffected. Carbon-doped Teflon® AF, or "black Teflon® AF," is a material well adapted for all or part of the walls of such a light-guiding flowcell for use in HPLC absorbance detection

BRIEF DESCRIPTION OF THE DRAWINGS

These and other features and advantages of the present invention will become more apparent from the following detailed description taken in conjunction with the accompanying drawings wherein like reference characters denote corresponding parts throughout the several views, and wherein.

DETAILED DESCRIPTION

A light-guiding structure that has superior signal to noise characteristics can be constructed if the absorption coefficient of the walls of the liquid containing vessel are judiciously chosen to only minimally attenuate the light guided through the liquid by internal reflection. The vessel may be formed to contain a single sample, as an array of single sample vessels or as flowcell capable of analyzing a sequence of samples. The basis of the invention is discussed utilizing as an example a light guiding flowcell which is simple and easy to construct, minimizes stray light and exhibits maximum light throughput for a chosen volume and pathlength. The low RI wall material is made sufficiently absorbing to block stray light paths that bypass part of or all of the liquid sample, a cause of nonlinearity between absorbance and concentration. The absence of masks or optical fibers inserted into the flowcell lumen allows optical throughput to be maximized.

The following discussion justifies the assertion that a bulk absorption coefficient for the low index wall material can be chosen such that undesired rays that enter the wall are absorbed, and yet desired rays, which are guided along the flowcell channel, are transmitted without loss. Absorption of light through a material is described by the Bouguer/Lambert law:

$$\frac{I}{I_0} = e^{-ab} \quad (3)$$

where $\alpha$ is the material absorption coefficient in units of reciprocal length, b is the distance traveled in the material and, ignoring end reflection losses, $I_0$ and I are the light intensity, or power, entering and leaving the material respectively.

Adequate light blocking can be achieved if the light transmitted through the tube wall, parallel to the lumen, is reduced to one part in 1,000 of the incident intensity, within a distance of 5 mm. This essentially eliminates stray light through the bulk material. With these parameters, Equation (3) yields an absorption coefficient of $\alpha=1.4$ mm$^{-1}$. The effect of this change in the material on the light-guiding properties is considered below.

Figure 4:
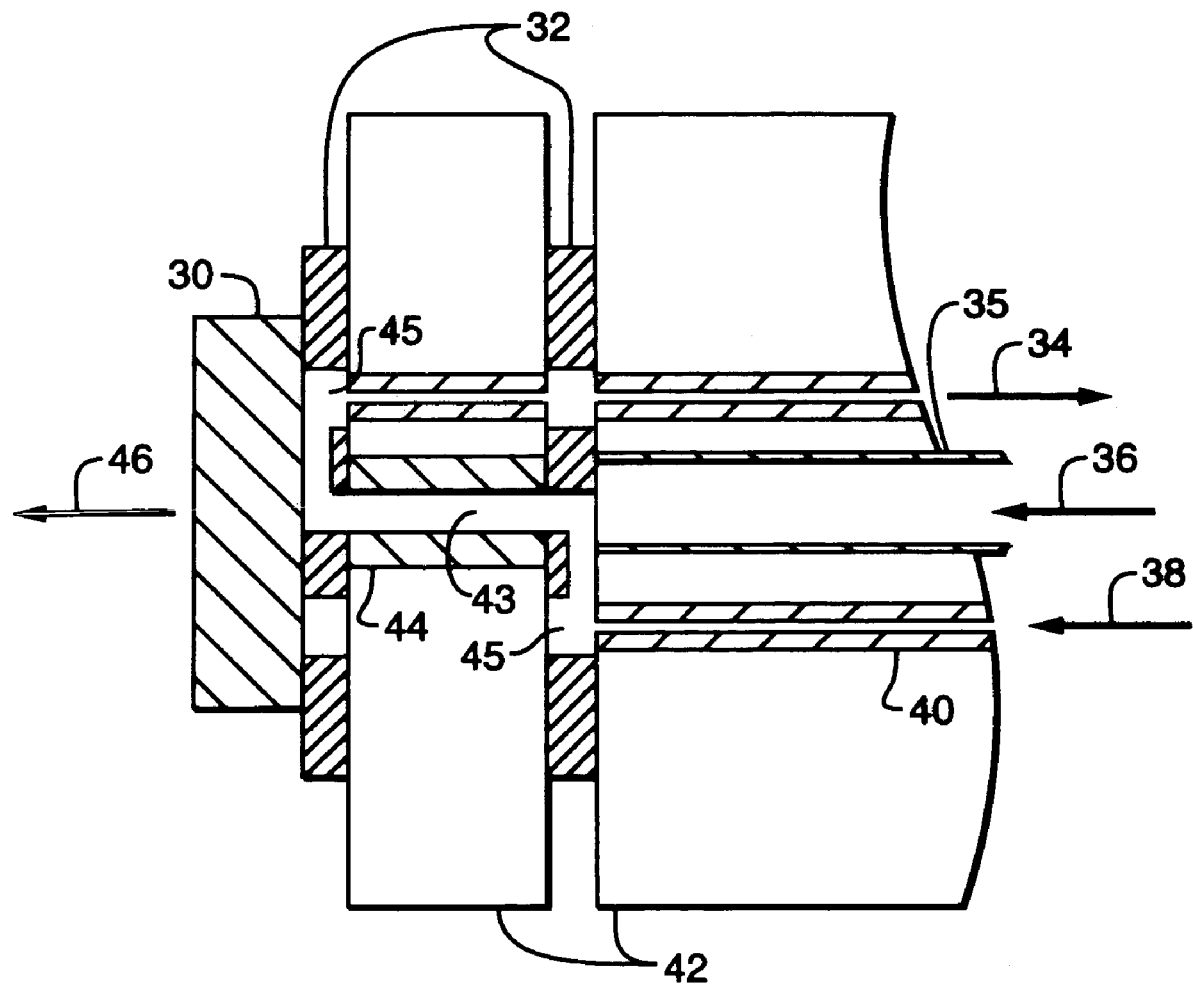
FIG. 4. is a diagram of a flowcell constructed incorporating the invention.

When light rays are guided by total internal reflection at the boundary between core material and a lower index cladding, there is a small penetration of light into the low index medium. If the low index medium is transparent, the internal reflection is 100%. But, if the low index medium absorbs light, some energy is trapped in the penetrating evanescent light wave and the process is referred to as attenuated total reflection (ATR). When absorption is low, as in the present design, relatively simple expressions can be used to calculate the effective thickness of Teflon® AF, penetrated by the light at each internal reflection (see Harrick N.J., Internal Reflection Spectroscopy, Harrick Scientific Corp., Ossining, N.Y., 1987, p 43). The effective thickness depends on the wavelength, angle of incidence, refractive index of the two media, and on the plane of polarization. The physical orientations of the components are illustrated in FIG. 4.

For light polarized perpendicular to the plane of incidence effective thickness is:

$$d_{e(perp)} = \frac{\lambda_1 n_{21} \cos\theta}{(\pi(1-n_{21}^2)(\sin^2\theta - n_{21}^2)^{1/2})} \quad (4a)$$

For light polarized parallel to the plane of incidence effective thickness is:

$$d_{e(parallel)} = \frac{\lambda_1 n_{21} \cos\theta(2\sin^2\theta - n_{21}^2)}{(\pi(1-n_{21}^2)\{(1+n_{21}^2)\sin^2\theta - n_{21}^2\}(\sin^2\theta - n_{21}^2)^{1/2})} \quad (4b)$$

where: $n_1$ is the refractive index of medium 1, the fluid sample $n_2$ is the refractive index of medium 2, the Teflon® AF in contact with the fluid $\theta$ is the angle of incidence of a ray internally reflected at the boundary between the two $n_{21} = n_2/n_1$ $\lambda_1 = \lambda/n_1$ is the wavelength in medium 1. $\lambda$ is the wavelength in air.

One possible application utilizes a 5 mm long light-guiding flowcell having an ID of 100 µm, a numerical aperture (NA) of the tube of 0.27 and a beam of light having a wavelength of 250 nm. The rays that make the largest angle with the axis (arcsin(NA)), and reflect from the boundary closest to the critical angle, make about ten reflections and penetrate the deepest into the wall. The effective thickness of Teflon® AF traversed by these rays is, assuming unpolarized light, the average of equations (4a) and (4b) above. For the worst case ray, the effective thickness is 1.4 µm per reflection or 14 µm for the full length of the flowcell. Using this value for b, and the value of $\alpha$ calculated above, equation (3) gives the transmittance of the guided light as 0.98. Rays making a smaller angle with the axis have an even higher transmittance. These calculations indicate that with this absorption coefficient, which is sufficiently large to block light transmitted through the darkened Teflon® AF wall, attenuation of the guided beam is negligible.

Figure 1:
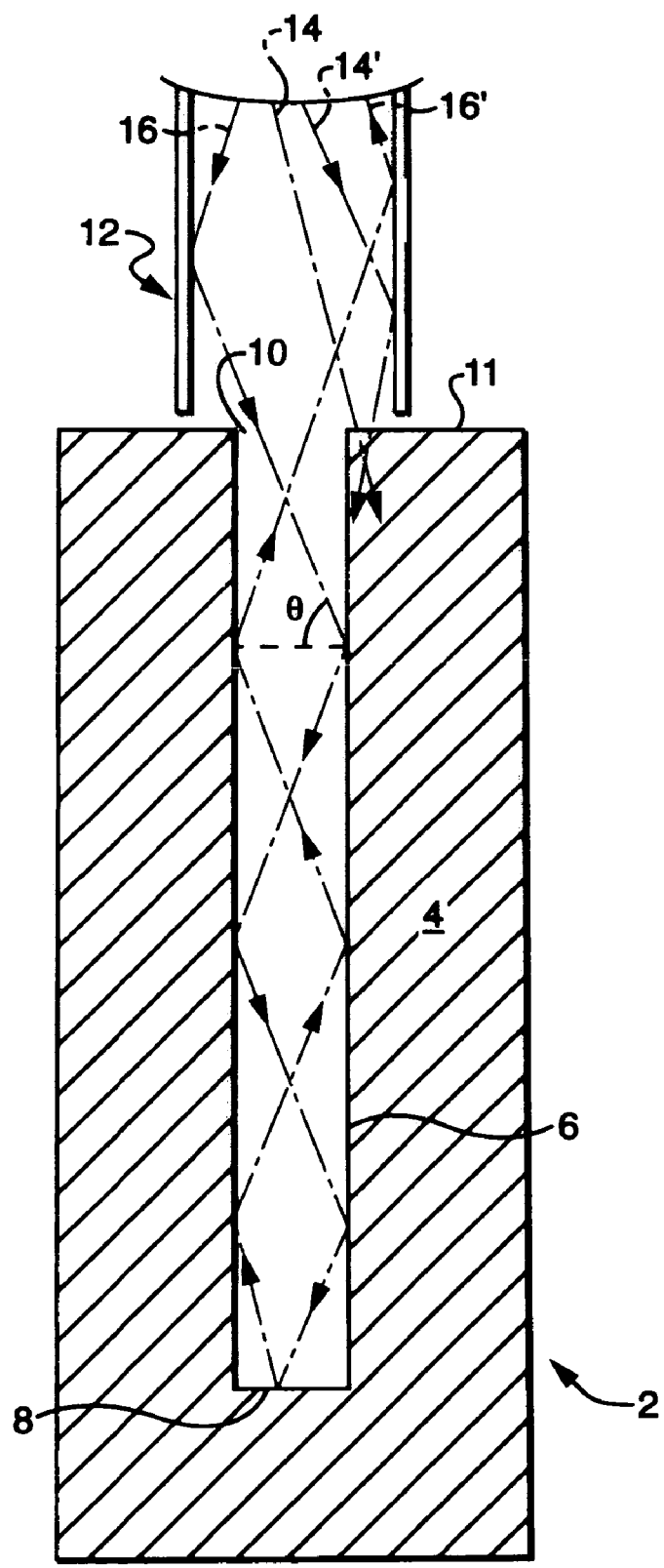
FIG. 1. is a simplified diagram of a light guiding vessel according to the invention.

FIG. 1 illustrates a single sample vessel 2 constructed using the invention for measuring light after it traverses the sample. The sample to be tested is placed in the cavity 6 of the vessel 2. An means for passage of light 10 is provided in the walls 4 of vessel 2 to allow light to enter 16 and exit 16'. The means for passage of light may be an opening, a window, a lens or an optic fiber. Since the walls 4 are formed of darkened Teflon® AF, light having an angle of incidence less than the critical angle, is guided down the cavity and some of the light is reflected off the end of the cavity to be measured as it exits the cavity. Light that impinges on the end surfaces 11 of the walls 4 is absorbed and does not interfere with the measurement. This vessel can be adapted for other configurations. An array of vessels 2 can be constructed to test multiple samples. If a window replaces reflecting surface 8, the measurement sensor can be placed opposite the light source. This adaptation may prove advantageous for high volume screening of discrete samples. When the vessel 2 is further modified to allow through passage of a sample fluid, a flowcell such as illustrated in FIG. 2 is formed.

Figure 2:
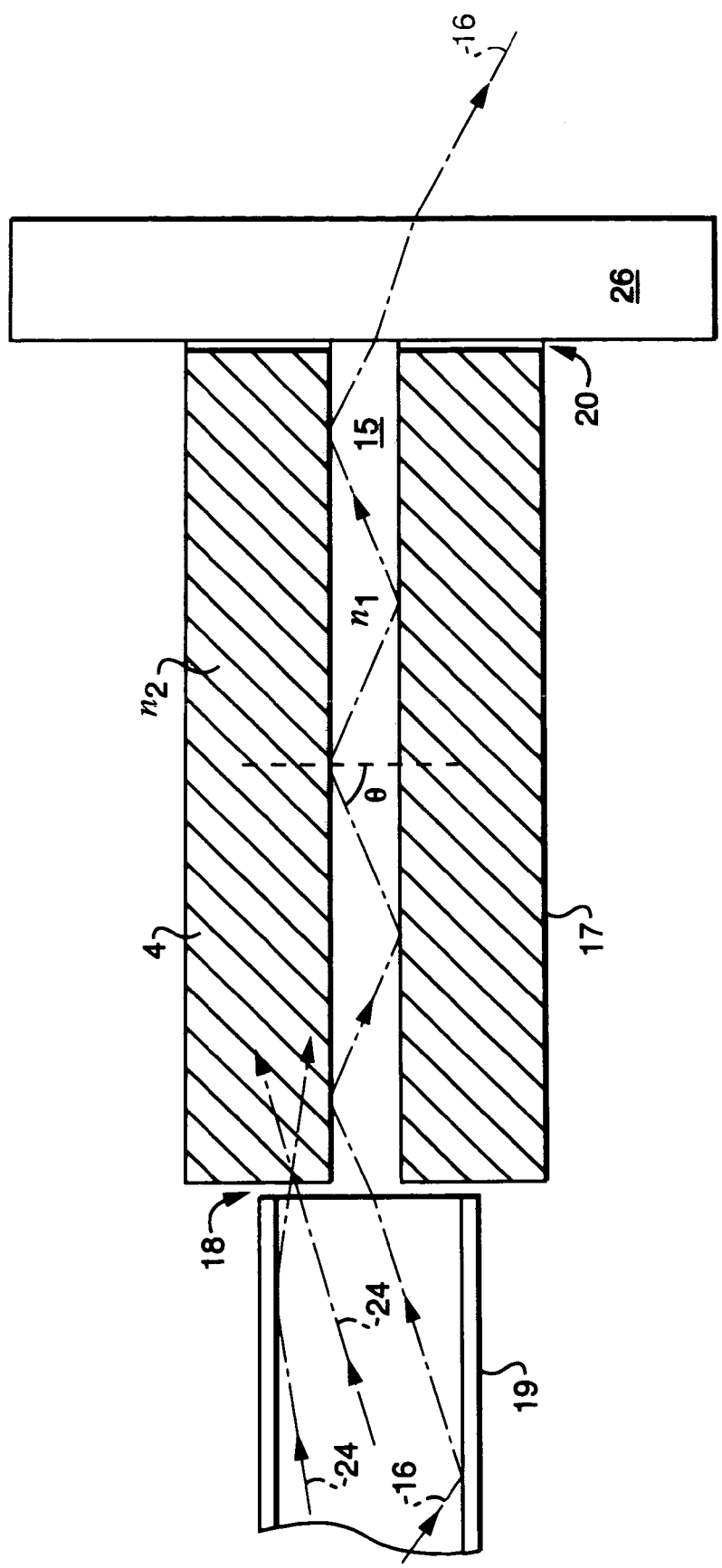
FIG. 2. is a simplified diagram of the light-guiding vessel in the form of a flowcell according to the invention.

FIG. 2 illustrates the simplified design of a flowcell made possible using this invention. Tube 17 has darkened Teflon® AF walls. Fluid under test enters at one end 18 of tube 17 and exits at the other end 19. Incident light 16, 24 is oriented at an angle within the NA of tube 17. The source of light 19 is wider than the ID of the tube 17 and is aligned with the axis. Light 16 that is oriented to enter the liquid medium having an RI of $n_1$ is guided down the cavity 15 because the angle of incidence, $\theta$, is less than the critical angle. Light 24 that falls outside the cavity enters the cell walls 4, travels a small distance, and is absorbed. FIG. 2 shows a simple window 26 at the exit of the light-guiding flowcell. This avoids matching and aligning an optical fiber to the flowcell exit and leads to better optical efficiency. The entrance to the flowcell can also be a window, with the light focused on the entrance. Rays hitting the walls 4 if the tube 17 are absorbed as above. The design is simplified because masks are no longer needed at the end of the cell. Optical efficiency is maximized because the whole of the fluid path cross-section can be flooded with light.

Figure 3:
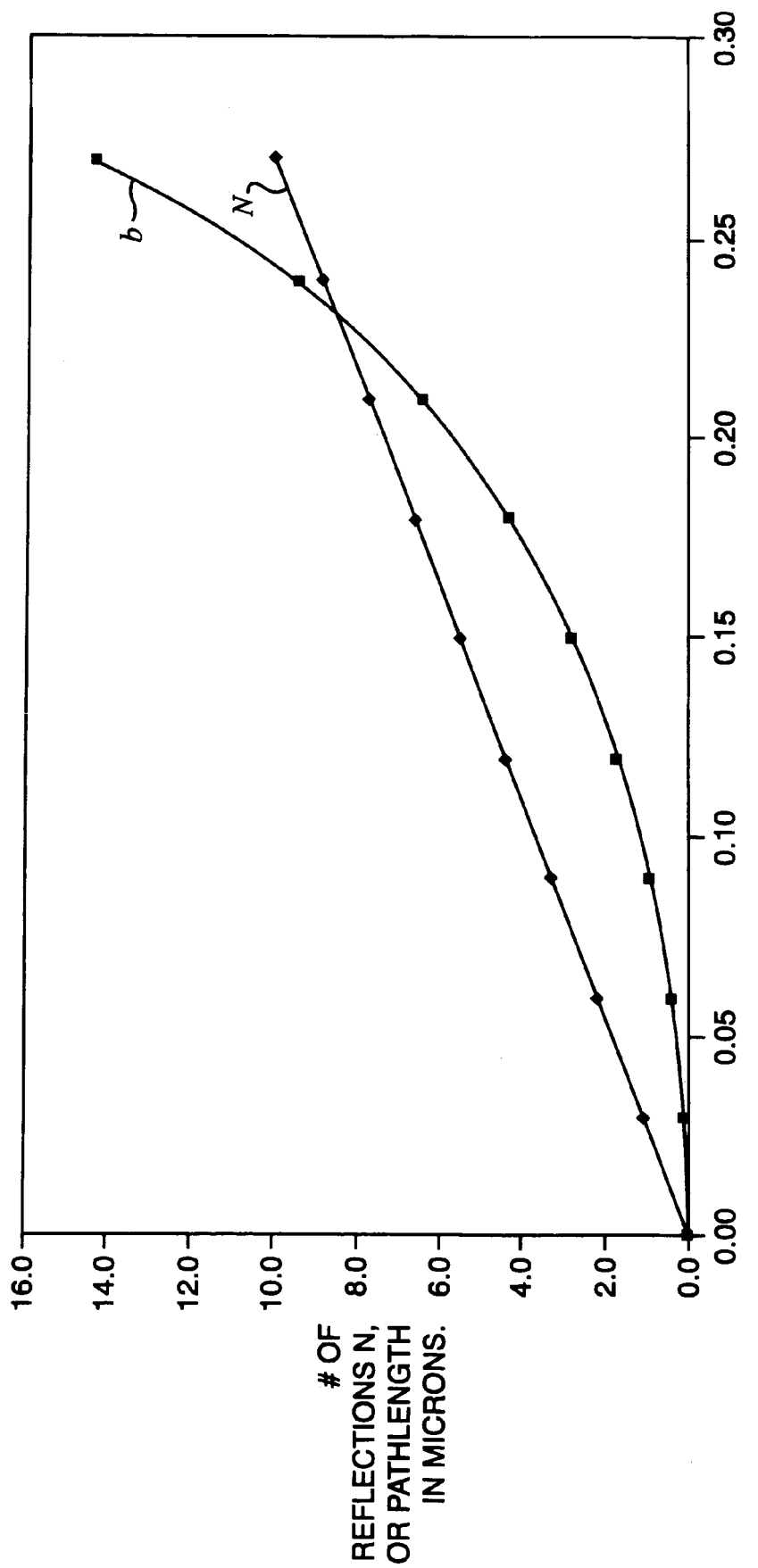
FIG. 3. is a graph illustrating the depth of penetration of a light wave into a wall according to the invention.

FIG. 3 shows the number of reflections (diamonds) made by a light wave undergoing total internal reflection from the inside wall of a Teflon® AF tube filled with water in the case calculated above to determine the effect on transmittance. Also plotted is the "effective thickness" (squares) of Teflon® AF material traversed by the light during its passage through the light guide. This enables the attenuation of a beam of light to be calculated as it makes multiple reflections down the tube. The data in FIG. 3 are plotted against numerical aperture, NA. NA defines the cone of rays entering the light guide. The most inclined ray makes an angle $\sin^{-1}(NA)$ with the axis in air external to the light guide. This is the guided ray which experiences the largest attenuation from wall absorption and is the one whose data are plotted in FIG. 3.

If ten times the concentration of black dopant were used, giving a wall absorption coefficient of $\alpha=14$ mm$^{-1}$, transmittance of the worst case ray would drop to 82%, a significant but tolerable loss. This allows reasonable latitude in selecting the concentration of the opaque dopant, or alternatively, allows the dopant absorption coefficient to vary by a factor of ten over the desired wavelength range and still meet the necessary criteria.

A preferred opaque dopant is chemically resistant to HPLC solvents and pH range, and has as flat a spectrum as possible over the wavelength region of interest, 200 to 800 nm. Carbon black has been incorporated into fused silica to make "black quartz" used to block stray light paths in flowcells and cuvettes, particularly those used to analyze fluorescence (See Hulme, U.S. Pat. No. 5,493,405; Fujita et al., U.S. Pat. No. 6,106,777). In these cells, no light guiding is involved because the wall material has a higher index than the analytical fluid. However, as a material which blocks transmitted light over a wide range of wavelengths, carbon is a good choice for the present application to light guided cells. Other materials could be used, such as finely divided metal particles. Many different dopants could be used over more restricted wavelength ranges.

FIG. 4 illustrates how a flowcell incorporating the invention may be constructed. The flowcell body 42 is constructed from a sealable material such as PEEK in multiple parts. The tube of darkened Teflon® AF 44 is supported in part of the cell body 42. Fluid 38 enters the body via capillary 40 and is brought to the tube cavity 43 by channels 45 etched in metal gaskets 32 between the body parts 42. After passing through the tube 44, fluid is further directed through the metal gaskets 32 and out a fluid port 34. Light 36 enters the flowcell via an optic fiber 35 so as to traverse the fluid-filled tube cavity 43. At the exit side of the tube 44, a window 30 allows light 46 to exit the flowcell toward the sensor. It is evident that light passes along the length of the light guiding tube 44. In this flowcell, the parts of the metal gaskets 32 that cover the ends of the tube walls 44 are not critical for light blocking because the opacity of the walls of tube 44 prevents stray light from entering the fluid path.

In one embodiment, finely-divided carbon black is mixed with Teflon® AF 2400 resin in powder form. The carbon black concentration is on the order of 0.01%-1%. In a preferred embodiment the carbon black concentration is approximately 0.1%. The resultant mixture is used to make "black" Teflon® AF tubing by extrusion or drawing using well-established methods. The low level of carbon black does not materially affect the ability to fabricate tubing. When the "black" Teflon® AF tubing is used in a light-guiding flowcell, it blocks the transmission of light through the cell walls so none of that stray light can reach the detector and cause errors in the measurement.

"Lab-on-a-chip" structures, where certain channels are fluidic connections, separation columns and reaction chambers have been produced on planar substrates. As a second embodiment of the present invention, strips of "black" Teflon® AF are extruded in ribbon form, several mm wide by about 1 mm thick. Sections of this are used as the substrate to form patterns of channels by, for example, hot embossing. Two such substrates bonded together, or one with an unstructured lid, are used to create "lab-on-a-chip" structures with unique properties. Some channels in the chip are used as fluidic connections to other channels formed as separation columns or the like. These can be connected to fluid containing light-guides created for detection. Windows into light-guiding sections are created and lengths of optical fiber bonded into the sandwich to bring the needed light onto the chip for attachment to the appropriate channel. Using opaque "black" Teflon® AF material as the substrate blocks stray light and allows light-guiding detection channels to be constructed. In addition, the "black" Teflon® AF bulk material prevents any stray light from the other sections of the chip from leaking light to the detection system. This improves detector linearity, as previously discussed. Use of the light-blocking substrate allows multiple light-guiding flowcells to be constructed on the same chip, without cross-talk.

Figure 5:
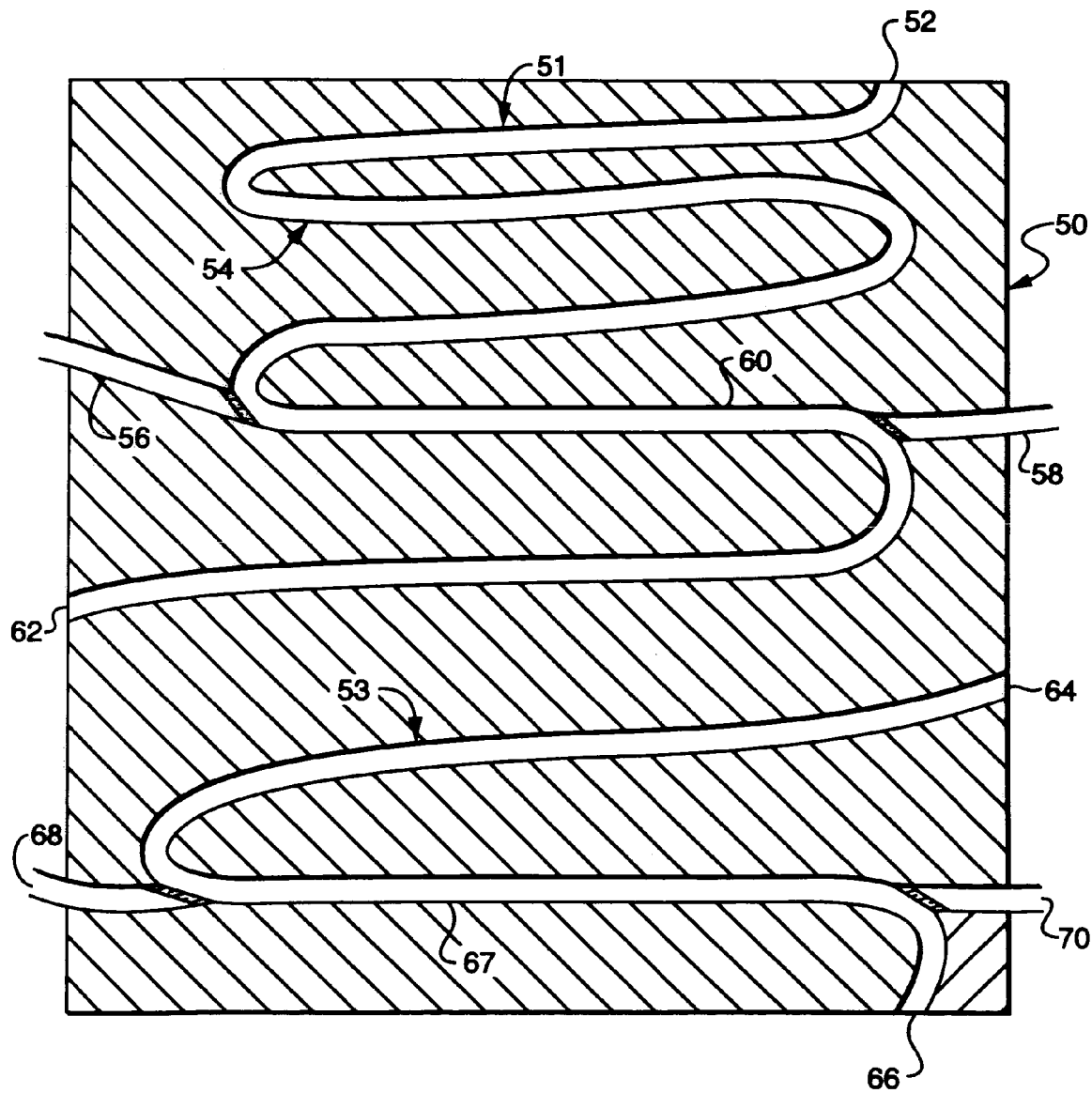
FIG. 5 is a simplified diagram of a "lab-on-a chip" implemented utilizing the invention.

FIG. 5 illustrates a simplified representation of a "lab-on-a-chip" made possible by the invention. Substrate 50 is formed from "black" Teflon® AF. Channel 51 forms a fluidic connection from an entrance 52 to a channel 54 formed as a separation column. Light fibers 56 and 58 are bonded so as to form part of the end walls of light guiding channel 60 used to measure the absorbance of a sample passing through channel 60. The fluid exits the structure through channel 62. On the same substrate, a separate light-guiding flowcell allows measurement the absorbance of a fluid passing through channel 53 to channel 67 which is the measurement channel. Separate light fibers 68, 70 are bonded to channel 67 to form the light entrance and exit. Because of the opacity of substrate 50, light is confined to the two light-guiding measurement channels 60, 67.

While the application of light-blocking low RI material has been discussed in the context of absorption measurement, the material is also applicable to light guiding applications used for fluorescence and Raman detection. The opaque cell walls absorb unwanted excitation light which enters or is scattered into the cell walls.

The material has been discussed in the context of a cuvette formed of an optically transparent material drawn into the form of a cylindrical thin-walled capillary as used in absorbance measurement. However, further applications of the "black" Teflon® AF form the cuvette into a container with a reflective surface opposite a light entering window/opening or a vessel with transparent windows opposite each other.

It is understood that various modifications may be made to the embodiments disclosed herein. Therefore, the above descriptions should not be considered limiting, but merely as exemplifications of the various embodiments. Those skilled in the art will envision other modifications within the scope and spirit of the claims appended hereto.

The invention claimed is:

1. A set of light-guiding flowcells for a fluid comprising: a set of channels formed in a substrate of material having an index of refraction lower than an index of said fluid and an absorption coefficient sufficient to substantially attenuate light propagating through said material; a set of channel covers formed in a section of material having an index of refraction identical to said substrate material and an absorption coefficient sufficient to substantially attenuate light propagating through said material, said set of channel covers fixed to said set of channels forming a set of covered channels; at least one covered channel having a fluid inlet and outlet port configured off an axis of said covered channel; at least one covered channel having a source of light at a light entrance end and having a light exit end; whereby said at least one covered channel and fluid effect guiding of said light by attenuated total reflection and said at least one covered channel has minimal absorptive effect on said light guided by internal reflection.

2. The set of light-guiding flowcells of claim 1 further comprising an optical fiber bonded to at least one covered channel providing said light source of light.

3. The set of light-guiding flowcells of claim 1 whereby the material forming said set of covered channels prevents light crosstalk between flowcells.

4. The set of light-guiding flowcells of claim 1 wherein at least one covered channel is configured as a separation column.

5. The set of light-guiding flowcells of claim 1 wherein at least one covered channel is configured as a fluidic connection.

6. The set of light-guiding flowcells of claim 1 wherein said substrate and said set of covered channels are formed of an amorphous fluoropolymer doped with a black dopant at a concentration of between 0.01-0.1% of the fluoropolymer.

7. The set of light-guiding flow cells of claim 6 wherein the back dopant is carbon black.

* * * * *

UNITED STATES PATENT AND TRADEMARK OFFICE
CERTIFICATE OF CORRECTION

PATENT NO. : 7,362,429 B2
APPLICATION NO. : 10/911126
DATED : April 22, 2008
INVENTOR(S) : Anthony C. Gilby It is certified that error appears in the above-identified patent and that said Letters Patent is hereby corrected as shown below:

Title page, Related U.S. Application Data should read

Item --(65) Continuation of PCT/US2003/05811, filed on Feb. 25, 2003, now abandoned.

(60) Provisional application No. 60/359,354, filed on February 25, 2002.--

Column 1, line 10 should read

--2003, abandoned, which claims priority to U.S. Provisional Patent Application--

Column 10, Line 7 should read

--channel providing said source of light.--

Signed and Sealed this

Twentieth Day of October, 2009

David J. Kappos
*Director of the United States Patent and Trademark Office*